(12) United States Patent
Zhang et al.

(10) Patent No.: US 8,980,947 B2
(45) Date of Patent: *Mar. 17, 2015

(54) CURING ACCELERATOR AND METHOD OF MAKING

(71) Applicant: Adhezion Biomedical, LLC, Wyomissing, PA (US)

(72) Inventors: Sheng Zhang, Hickory, NC (US); Rafael Ruiz, Sr., Hudson, NC (US); Max Azevedo, Alpharetta, GA (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/230,351

(22) Filed: Mar. 31, 2014

(65) Prior Publication Data

US 2014/0328788 A1 Nov. 6, 2014

Related U.S. Application Data

(63) Continuation of application No. 11/767,565, filed on Jun. 25, 2007, now Pat. No. 8,729,121.

(51) Int. Cl.
| | | |
|---|---|---|
| *A61K 31/275* | (2006.01) | |
| *A61L 24/06* | (2006.01) | |
| *A61L 24/00* | (2006.01) | |

(52) U.S. Cl.
CPC ............. *A61L 24/06* (2013.01); *A61L 24/0015* (2013.01)
USPC ........................................................ 514/526

(58) Field of Classification Search
CPC . A61L 26/0014; A61L 26/0066; A61L 24/06; A61L 24/0015; A61K 13/74; A61K 13/765; A61K 13/78; A61K 13/785; A61K 13/275
See application file for complete search history.

(56) References Cited

U.S. PATENT DOCUMENTS

| | | |
|---|---|---|
| 211,104 A | 1/1879 | Mulford |
| 334,046 A | 1/1886 | Pinkham |
| 1,221,227 A | 4/1917 | Schulz |
| 1,229,195 A | 6/1917 | Hamilton |
| 1,234,844 A | 7/1917 | Williams |
| 1,822,566 A | 9/1931 | Davies |
| 2,333,070 A | 10/1943 | Hoey et al. |
| 2,721,858 A | 10/1955 | Joyner et al. |
| 2,794,788 A | 6/1957 | Coover, Jr. et al. |
| 2,912,454 A | 11/1959 | McKeever |
| 3,152,352 A | 10/1964 | Kosik, Jr. |
| 3,254,111 A | 5/1966 | Hawkins et al. |
| 3,260,637 A | 7/1966 | von Bramer |
| 3,282,773 A | 11/1966 | Wicker, Jr. et al. |
| 3,324,855 A | 6/1967 | Heimlich |
| 3,393,962 A | 7/1968 | Andrews |
| 3,451,538 A | 6/1969 | Trementozzi |
| 3,523,628 A | 8/1970 | Colvin et al. |
| 3,524,537 A | 8/1970 | Winter |
| 3,527,224 A | 9/1970 | Rabinowitz |
| 3,527,841 A | 9/1970 | Wicker, Jr. et al. |
| 3,540,577 A | 11/1970 | Trementozzi et al. |
| 3,564,078 A | 2/1971 | Wicker, Jr. et al. |
| 3,579,628 A | 5/1971 | Gander et al. |
| 3,607,542 A | 9/1971 | Leonard et al. |
| 3,614,245 A | 10/1971 | Schwartzman |
| 3,667,472 A | 6/1972 | Halpern |
| 3,692,752 A | 9/1972 | Setsuda et al. |
| 3,742,018 A | 6/1973 | O'Sullivan |
| 3,779,706 A | 12/1973 | Nablo |
| 3,797,706 A | 3/1974 | Mule |
| 3,836,377 A | 9/1974 | Delahunty |
| 3,863,014 A | 1/1975 | Mottus |
| 3,903,055 A | 9/1975 | Buck |

(Continued)

FOREIGN PATENT DOCUMENTS

| | | |
|---|---|---|
| DE | 4009621 | 10/1991 |
| DE | 20103336 | 5/2001 |
| DE | 102007019044 | 10/2008 |
| EP | 0127466 | 12/1984 |
| EP | 0271675 | 6/1988 |

(Continued)

OTHER PUBLICATIONS

"Aclar.RTM./Barex.RTM. Laminates: Flexible Solutions for Pharma Packaging" Drug Delivery Technology vol. 3, No. 3, May 2003, Posted on Mar. 28, 2008, http://www.drugdeliverytech.com/ME2/dirmod.asp?sid=&nm=&type=Publis-hing&mod=Publications%3A%.

(Continued)

*Primary Examiner* — Susan Tran
*Assistant Examiner* — Jessica Worsham
(74) *Attorney, Agent, or Firm* — Baker & Hostetler LLP

(57) ABSTRACT

A sterilized cyanoacrylate adhesive composition including a cyanoacrylate composition and a cure speed enhancer, wherein the sterilized cyanoacrylate adhesive composition does not cure upon sterilization. A kit for applying the sterilized cyanoacrylate adhesive composition, including the cyanoacrylate adhesive composition and an applicator. A method of making the sterilized cyanoacrylate adhesive composition, by adding a cure speed enhancer to a cyanoacrylate adhesive composition and sterilizing the composition. A method of applying the sterilized cyanoacrylate adhesive composition to tissue by applying the sterilized cyanoacrylate adhesive composition as a liquid, and quickly curing the sterilized cyanoacrylate adhesive composition. A method of sealing tissue by applying the sterilized cyanoacrylate adhesive composition as a liquid to tissue to be sealed, quickly curing the sterilized cyanoacrylate adhesive composition, and sealing the tissue.

21 Claims, No Drawings

(56) References Cited

U.S. PATENT DOCUMENTS

| | | |
|---|---|---|
| 3,924,623 A | 12/1975 | Avery |
| 3,941,488 A | 3/1976 | Maxwell |
| 3,975,422 A | 8/1976 | Buck |
| 3,995,641 A | 12/1976 | Kronenthal et al. |
| 4,003,942 A | 1/1977 | Buck |
| 4,012,402 A | 3/1977 | Buck |
| 4,013,703 A | 3/1977 | Buck |
| 4,038,345 A | 7/1977 | O'Sullivan et al. |
| 4,041,063 A | 8/1977 | Buck |
| 4,042,442 A | 8/1977 | Dombroski et al. |
| 4,057,535 A | 11/1977 | Lipatova et al. |
| 4,102,945 A | 7/1978 | Gleave |
| 4,105,715 A | 8/1978 | Gleave |
| 4,109,037 A | 8/1978 | Nohara |
| 4,142,630 A | 3/1979 | Hayes et al. |
| 4,170,585 A | 10/1979 | Motegi et al. |
| 4,171,416 A | 10/1979 | Motegi et al. |
| 4,182,823 A | 1/1980 | Schoenberg |
| 4,265,948 A | 5/1981 | Hayes et al. |
| 4,310,509 A | 1/1982 | Berglund et al. |
| 4,323,557 A | 4/1982 | Rosso et al. |
| 4,328,170 A | 5/1982 | Okawara et al. |
| 4,340,043 A | 7/1982 | Seymour |
| 4,364,876 A | 12/1982 | Kimura et al. |
| 4,374,126 A | 2/1983 | Cardarelli et al. |
| 4,377,490 A | 3/1983 | Shiraishi et al. |
| 4,386,193 A | 5/1983 | Reich et al. |
| 4,413,753 A | 11/1983 | Stock |
| 4,439,196 A | 3/1984 | Higuchi |
| 4,444,933 A | 4/1984 | Columbus et al. |
| 4,447,224 A | 5/1984 | DeCant, Jr. et al. |
| 4,447,233 A | 5/1984 | Mayfield |
| 4,460,759 A | 7/1984 | Robins |
| 4,475,916 A | 10/1984 | Himmelstein |
| 4,480,940 A | 11/1984 | Woodruff |
| 4,486,194 A | 12/1984 | Ferrara |
| 4,487,603 A | 12/1984 | Harris |
| 4,533,422 A | 8/1985 | Litke |
| 4,542,012 A | 9/1985 | Dell |
| 4,551,366 A | 11/1985 | Maruhashi et al. |
| 4,554,686 A | 11/1985 | Baker |
| 4,643,181 A | 2/1987 | Brown |
| 4,646,765 A | 3/1987 | Cooper et al. |
| 4,649,909 A | 3/1987 | Thompson |
| 4,652,763 A | 3/1987 | Nablo |
| 4,685,591 A | 8/1987 | Schaefer et al. |
| 4,713,235 A | 12/1987 | Krall |
| 4,718,966 A | 1/1988 | Harris et al. |
| 4,772,148 A | 9/1988 | Buschemeyer |
| 4,786,534 A | 11/1988 | Aiken |
| 4,818,325 A | 4/1989 | Hiraiwa et al. |
| 4,925,678 A | 5/1990 | Ranney |
| 4,959,217 A | 9/1990 | Sanders et al. |
| 4,977,892 A | 12/1990 | Ewall |
| 4,978,527 A | 12/1990 | Brink et al. |
| 4,994,542 A | 2/1991 | Matsuda et al. |
| 5,009,654 A | 4/1991 | Minshall et al. |
| 5,039,753 A | 8/1991 | Woods et al. |
| 5,042,690 A | 8/1991 | O'Meara |
| 5,051,256 A | 9/1991 | Barnes |
| 5,069,907 A | 12/1991 | Mixon et al. |
| 5,083,685 A | 1/1992 | Amemiya et al. |
| 5,131,777 A | 7/1992 | Kimura et al. |
| 5,135,964 A | 8/1992 | Lee et al. |
| 5,167,616 A | 12/1992 | Haak et al. |
| 5,169,383 A | 12/1992 | Gyory et al. |
| 5,192,536 A | 3/1993 | Huprich |
| 5,225,182 A | 7/1993 | Sharma |
| 5,232,774 A | 8/1993 | Otsuka et al. |
| 5,236,703 A | 8/1993 | Usala |
| 5,240,525 A | 8/1993 | Percec et al. |
| 5,254,132 A | 10/1993 | Barley et al. |
| 5,283,034 A | 2/1994 | Okrongly et al. |
| 5,288,159 A | 2/1994 | Wirt |
| 5,302,629 A | 4/1994 | Berejka |
| 5,306,490 A | 4/1994 | Barley, Jr. |
| 5,312,864 A | 5/1994 | Wenz et al. |
| 5,328,687 A | 7/1994 | Leung et al. |
| 5,344,670 A | 9/1994 | Palmer et al. |
| 5,350,798 A | 9/1994 | Linden et al. |
| 5,358,349 A | 10/1994 | Burroughs et al. |
| 5,370,221 A | 12/1994 | Magnusson et al. |
| 5,403,591 A | 4/1995 | Tighe et al. |
| 5,411,345 A | 5/1995 | Ueji et al. |
| 5,453,457 A | 9/1995 | Meltzer et al. |
| 5,457,141 A | 10/1995 | Matsuda et al. |
| 5,470,597 A | 11/1995 | Mendenhall |
| 5,475,110 A | 12/1995 | Hudkins et al. |
| 5,480,935 A | 1/1996 | Greff et al. |
| 5,530,037 A | 6/1996 | McDonnell et al. |
| 5,547,662 A | 8/1996 | Khan et al. |
| 5,561,198 A | 10/1996 | Huver et al. |
| 5,665,817 A | 9/1997 | Greff et al. |
| 5,684,042 A | 11/1997 | Greff et al. |
| 5,730,994 A | 3/1998 | Askill et al. |
| 5,749,956 A | 5/1998 | Fisher et al. |
| 5,762,919 A | 6/1998 | Greff et al. |
| 5,783,177 A | 7/1998 | Greff et al. |
| 5,803,086 A | 9/1998 | Scholz et al. |
| 5,807,563 A | 9/1998 | Askill et al. |
| 5,811,091 A | 9/1998 | Greff et al. |
| 5,874,044 A | 2/1999 | Kotzev |
| 5,902,594 A | 5/1999 | Greff et al. |
| 5,916,882 A | 6/1999 | Jeng |
| 5,928,611 A | 7/1999 | Leung |
| 5,944,754 A | 8/1999 | Vacanti |
| 5,957,877 A | 9/1999 | Askill et al. |
| 5,979,450 A | 11/1999 | Baker et al. |
| 5,981,621 A | 11/1999 | Clark et al. |
| 5,985,395 A | 11/1999 | Comstock et al. |
| 5,998,472 A | 12/1999 | Berger et al. |
| 6,086,906 A | 7/2000 | Greff et al. |
| 6,090,397 A | 7/2000 | Lee et al. |
| 6,099,807 A | 8/2000 | Leung |
| 6,136,326 A | 10/2000 | Kotzev |
| 6,143,352 A | 11/2000 | Clark et al. |
| 6,143,805 A | 11/2000 | Hickey et al. |
| 6,155,265 A | 12/2000 | Hammerslag |
| 6,214,332 B1 | 4/2001 | Askill et al. |
| 6,217,603 B1 | 4/2001 | Clark et al. |
| 6,228,354 B1 | 5/2001 | Jeng |
| 6,245,933 B1 | 6/2001 | Malofsky et al. |
| 6,248,800 B1 | 6/2001 | Greff et al. |
| 6,294,629 B1 | 9/2001 | O'Dwyer et al. |
| 6,299,631 B1 | 10/2001 | Shalaby |
| 6,310,166 B1 | 10/2001 | Hickey et al. |
| 6,316,523 B1 | 11/2001 | Hyon et al. |
| 6,323,275 B2 | 11/2001 | Takahashi et al. |
| 6,352,704 B1 | 3/2002 | Nicholson et al. |
| 6,488,665 B1 | 12/2002 | Severin et al. |
| 6,492,434 B1 | 12/2002 | Barley, Jr. et al. |
| 6,495,229 B1 | 12/2002 | Carte et al. |
| 6,547,917 B1 | 4/2003 | Misiak et al. |
| 6,579,469 B1 | 6/2003 | Nicholson et al. |
| 6,620,846 B1 | 9/2003 | Jonn et al. |
| 6,626,296 B1 | 9/2003 | Jimu et al. |
| 6,667,031 B2 | 12/2003 | Azevedo |
| 6,699,940 B2 | 3/2004 | Shalaby |
| 6,742,522 B1 | 6/2004 | Baker et al. |
| 6,743,858 B2 | 6/2004 | Hickey et al. |
| 6,746,667 B2 | 6/2004 | Badejo et al. |
| 6,767,552 B2 | 7/2004 | Narang |
| 6,779,657 B2 | 8/2004 | Mainwaring et al. |
| 6,797,107 B1 | 9/2004 | Kotzey |
| 6,802,416 B1 | 10/2004 | D'Alessio et al. |
| 6,849,082 B2 | 2/2005 | Azevedo |
| 6,881,421 B1 | 4/2005 | da Silveira et al. |
| 6,896,838 B2 | 5/2005 | D'Alessio |
| 6,942,875 B2 | 9/2005 | Hedgpeth |
| 6,960,040 B2 | 11/2005 | D'Alessio et al. |
| 6,974,585 B2 | 12/2005 | Askill |
| 6,977,278 B1 | 12/2005 | Misiak |
| 6,995,227 B2 | 2/2006 | Ryan et al. |
| 7,255,874 B1 | 8/2007 | Bobo et al. |

(56) References Cited

U.S. PATENT DOCUMENTS

| | | |
|---|---|---|
| 2002/0002223 A1 | 1/2002 | Cox et al. |
| 2002/0037272 A1 | 3/2002 | Askill et al. |
| 2003/0044380 A1 | 3/2003 | Zhu et al. |
| 2003/0077386 A1 | 4/2003 | Azevedo |
| 2003/0135016 A1 | 7/2003 | Tajima et al. |
| 2003/0158579 A1 | 8/2003 | Azevedo |
| 2003/0158580 A1 | 8/2003 | Azevedo |
| 2004/0115274 A1 | 6/2004 | Cox et al. |
| 2004/0126355 A1 | 7/2004 | Childers |
| 2004/0127738 A1 | 7/2004 | Azevedo |
| 2004/0253039 A1 | 12/2004 | Stenton |
| 2005/0042266 A1 | 2/2005 | Narang |
| 2005/0047846 A1 | 3/2005 | Narang et al. |
| 2005/0067312 A1 | 3/2005 | Gupta et al. |
| 2005/0142163 A1 | 6/2005 | Hunter et al. |
| 2005/0147582 A1 | 7/2005 | Zimmerman et al. |
| 2005/0182347 A1 | 8/2005 | Bishop et al. |
| 2005/0196431 A1 | 9/2005 | Narang et al. |
| 2005/0197421 A1 | 9/2005 | Loomis |
| 2005/0281866 A1 | 12/2005 | Jarrett et al. |
| 2005/0284487 A1 | 12/2005 | Gellerstedt et al. |
| 2006/0062687 A1 | 3/2006 | Morales |
| 2006/0188486 A1 | 8/2006 | Carpenter et al. |
| 2007/0041935 A1 | 2/2007 | Salamone et al. |
| 2007/0048356 A1 | 3/2007 | Schorr et al. |
| 2007/0078207 A1 | 4/2007 | Jonn et al. |
| 2007/0092481 A1 | 4/2007 | Misiak et al. |
| 2007/0092483 A1 | 4/2007 | Pollock |
| 2007/0147947 A1 | 6/2007 | Stenton et al. |
| 2007/0299043 A1 | 12/2007 | Hunter et al. |
| 2008/0021139 A1 | 1/2008 | Blacklock et al. |
| 2008/0078413 A1 | 4/2008 | Padget et al. |
| 2008/0102053 A1 | 5/2008 | Childers |
| 2009/0022779 A1 | 1/2009 | Kelly et al. |
| 2009/0317353 A1 | 12/2009 | Zhang et al. |
| 2010/0035997 A1 | 2/2010 | Broadley |
| 2010/0269749 A1 | 10/2010 | Badejo et al. |

FOREIGN PATENT DOCUMENTS

| | | |
|---|---|---|
| FR | 2700698 | 7/1994 |
| GB | 1230560 | 5/1971 |
| GB | 2200124 | 7/1988 |
| JP | 59/066471 | 4/1984 |
| JP | 62/022877 | 1/1987 |
| JP | 03/207778 | 9/1991 |
| JP | 10/140091 | 5/1998 |
| WO | WO 96/14292 | 5/1996 |
| WO | WO 96/23532 | 8/1996 |
| WO | WO 99/10020 | 3/1999 |
| WO | WO 03/070257 | 8/2003 |
| WO | WO 2004/045498 | 6/2004 |
| WO | WO 2006/073922 | 7/2006 |
| WO | WO 2009/064291 | 5/2009 |

OTHER PUBLICATIONS

"Answer and Counterclaim", *Adhezion Biomedical, LLC v. Max Azevedo*, Civil Action No. 13-CVS-191, State of North Carolina, Superior Court Division, Mar. 20, 2013, 16 pages.

"Complaint", *Adhezion Biomedical, LLC v. Max Azevedo*, Civil Action No. 13-CVS-191, State of North Carolina, Superior Court Division, filed Feb. 13, 2013,17 pages.

"Consent Judgment", *Adhezion Biomedical, LLC v. Max Azevedo*, Civil Action No. 13-CV-191, State of North Carolina, Superior Court Division, Jul. 24, 2013, 7 pages.

"First Amended Answer and Counterclaim", *Adhezion Biomedical, LLC v. Max Azevedo*, Civil Action No. 13-CVS-191, State of North Carolina, Superior Court Division, Apr. 29, 2013, 17 pages.

"Reply and Defenses to Counterclaim", *Adhezion Biomedical, LLC v. Max Azevedo*, Civil Action No. 13-CV-191, State of North Carolina, Superior Court Division, Jun. 3, 2013, 12 pages.

Bhatia et al, "Topical Phenytoin for Wound Healing" Dermatology Online Journal, 10(1): Jul. 5, 2004, 6 pages as downloaded from http://! dermatology-s 10 .cdlib.org/101/reviews/phenytoin/bhatia.html.

Borrel et al. "The Effect of Crown Ethers, Tetraalkylammonioum Salts, and Polyoxyethylene Amphiphiles on Pirarubicin Incorporation in K562 Resistant Cells" Biochemical Pharmacology, vol. 50, No. 12., pp. 2069-2076, 1995.

Cameron, J.L. et al., "Degradation of Cyanoacrylate Tissue Adhesive, pt. 1", Surgery, vol. 58, Iss. 2, Aug. 1965, pp. 424-430.

Collins et al., "Biological Substrates and Cure Rates of Cyanoacrylate Tissue Adhesives" Archives of Surgery vol. 93, Sep. 1966, 428-432.

Darwish et al., "The evaluation of crown ether based niosomes as cation containing and cation sensitive drug delivery systems" International Journal of Pharmaceutics 159 (1997) 207-213.

Dumont et al., "New Oligosaccharidic Crown Ethers as Potential Drug-Targetting Vectors: Synthesis & Biological Evaluation" Bioorganic & Medicinal Chemistry Letters, vol. 4, No. 9, pp. 1123-1126, 1994.

Fussnegger, B. "Poloxamers (1) Lutrol.RTM. F 68 (Poloxamer 188)." BASF ExAct, Nov. 5-6, 1999.

Garnier-Suillerot et al., "Analysis of Drug Transport Kinetics in Multidrug-resistant Cells: Implications for Drug Action" Current Medicinal Chemistry, 2001, 8 51-64.

Hansen, "Fast Cure—High moisture vapor transmission rate adhesives improve wound care." Adhesives Age Mar. 22-25, 2003.

http://www.merriam-webster.com/dictionary/kit.

International Search Report and Written Opinion issued Jan. 9, 2012 for corresponding international patent application No. PCT/US2011/047090.

Lehman et al., "Toxicity of Alkyl 2-Cyanoacrylates", Archives of Surgery, vol. 93, Issue 3, Sep. 1966, pp. 441-446.

Leonard, F, "Hemostatic Applications of Alpha Cyanoacrylates: Bonding Mechanism and Physiological Degradation of Bonds", Adhesion in Biological Systems, ed. R.S. Manly, 1970, pp. 185-199.

Leonard, F. et al., "Interfacial Polymerization of n-Alkyl a-Cyanoacrylate Homologs", Journal of Applied Polymer Science, vol. 10 1966, pp. 1617-1623.

Leonard, F. et al., "Synthesis and Degradation of Poly (alkyl a-Cyanoacrylates)", Journal of Applied Polymer Science, vol. 10, Iss 8, Aug. 1966, p. 1214.

Leonard, F. et al., "Synthesis and Degradation of Poly(alkyl a-Cyanoacrylates)", Journal of Applied Polymer Science, vol. 10, Iss. 2, Feb. 1966, pp. 259-272.

Material Safety Data Sheet (MSDS) of 2-octyl cyanoacrylate; Jun. 2, 2004.

Material Safety Data Sheet (MSDS) of isobuthyl-2-cyanoacrylate; Sep. 25, 1998.

Material Safety Data Sheet (MSDS) of n-butyl cyanoacrylate; Oct. 19, 2009 and Jun. 2, 2004.

Naeini et al, "Effects of Topical and Parenteral Application of Phenytoin on Cutaneous Wound Healing in Rabbits" in Journal of Animal and Veterinary Advances 2008, 7(12),1537-1545.

Pendse etal, "Topical Phenytoin in Wound Healing" International Journal of Dermatology, Mar. 1993, 32(3), 214-217.

Quinn et al, "A Randomized Trial Comparing Octylcyanoacrylate Tissue Adhesive and Sutures in the Management of Lacerations" JAMA , May 21, 1997, 277(19),1527-1530.

Scheinfeld, "Phenytoin in Cutaneous Medicine: Its Uses, Mechanisms and Side Effects" Dermatology Online Journal, Aug. 2003, 9(3), 6, 17pages) downloaded from http://dermatology-s1 O.cdlib.org/93/reviews/dilantin/scheinfeld.html.

Shapiro, "Acceleration of Gingival Wound Healing in Non-Epileptic Patients Receiving Diphenylhydantoin Sodium (Dilantin, Epanutin)" in Exp. Med. Surg. 1958, 16(I), 41-53.

Simon et al, "Lacerations Against Langer's Lines: To Glue or Suture" in Journal of Emergency Medicine, Mar. 4, 1998, 16(2),185-189.

Talas et al, "Role of Phenytoin in Wound Healing—A Wound Pharmacology Perspective" in Biochemical Phannacology, May 1999, 57, 1085-1094.

(56) References Cited

OTHER PUBLICATIONS

Tseng, Y.C. et al., "Modification of synthesis and investigation of properties for 2-cyanoacrylates", Biomaterials, vol. 11, Jan. 1990, pp. 73-79.

Uchegbu et al., "Non-ionic surfactant based vesicles (niosomes) in drug delivery" International Journal of Pharmaceutics 172 (1998) 33-70.

Vezin, W.R. et al., "Diffusion of Small Molecules in Poly-n-Alkyl Cyanoacrylates", British Pharmaceutical Conference 1978—Communications presented at the 115th meeting, Coventry, Sep. 11-15, 1978, Journal of Pharmacy and Pharmacology, vol. 30, Issue: Suppl, Dec. 1978, p. 2P.

Vezin, W.R. et al., "In vitro heterogeneous degradation of poly(n-alkyl a-cyanoacrylates)", Journal of Biomedical Materials Research, vol. 14, 1980, pp. 93-106.

Woodward, S.C. et al., "Histotoxicity of Cyanoacrylate Tissue Adhesives in the Rat", Annals of Surgery, vol. 162, No. 1, Jul. 1965, pp. 113-122.

Yonezawa, M. et al., "Studies on a-Cyanoacrylate, VI: Reaction of Cyanoacetate with Formaldehyde" Yuki Gosei Kagaku Kyokaishi, vol. 25, Iss 4, Apr. 1967, pp. 311-316.

CURING ACCELERATOR AND METHOD OF MAKING

CROSS REFERENCE TO RELATED APPLICATIONS

The present application is a continuation of U.S. patent application Ser. No. 11/767,565, filed Jun. 25, 2007, which is hereby incorporated by reference in its entirety.

BACKGROUND OF THE INVENTION (1) Field of the Invention

The present invention relates to cyanoacrylate adhesives. In particular, the present invention relates to cyanoacrylate adhesives with a super cure speed for medical use.

(2) Description of Related Art

Cyanoacrylate compositions have long been known in the art as excellent adhesives. The cyanoacrylate adhesives are liquid monomers that polymerize on contact with tissue surfaces in an exothermic reaction creating a strong yet flexible film. The polymer film is generally formed rapidly. Liquid cyanoacrylate compositions have found application in medicine for closing wounds and incisions, especially in cases where suturing does not provide satisfactory results because of cyanoacrylate's unique ability to bond living tissue and their long-term bond strength. They have found wide applications as industrial and structural adhesives, consumer products for repair of household items and in the hobby sector for assembly and repair.

It is well known that cyanoacrylate adhesive compositions are very sensitive and careful handling is required to prepare their formulations. In order to extend the applications of cyanoacrylate adhesives, a variety of additives have been incorporated in their formulations including stabilizers, viscosity modifiers, thixotropic agents, plasticizers, biocompatible agents, and polymerization activators.

Cyanoacrylate polymerization is usually considered as the result of an anionic initiation with water being a sufficiently strong base. In spite of the relatively fast cure speed of cyanoacrylate adhesives, polymerization enhancers have to be incorporated for specific applications. First, the cure speed would be drastically dropped if cyanoacrylate adhesives were applied to the acidic substrates such as wood and paper. In this case, the cyanoacrylate adhesives with a faster cure time would offer an option. In addition, a relatively large amount of cyanoacrylate applied in certain cases will result in the slower hardening throughout the adhesives. However, a better cure-through-gap performance should be attained if a faster curing cyanoacrylate formulation is used.

In order to enhance the polymerization rate for such applications, a number of efforts have been made by applying accelerators through different methods. For example, a two component system has been used by packaging the cyanoacrylate adhesive and the accelerator separately. The cure speed of cyanoacrylate adhesives is improved. The disadvantage of this method is that the accurate measurement and mixing two components homogenously are very difficult tasks to achieve since only a tiny amount of accelerators is generally required.

As an example, U.S. Pat. No. 5,928,611 to Leung discloses an applicator tip for dispensing a polymerizable material, in which a polymerization accelerator was included. The accelerator initiates polymerization when the polymerizable material is dispensed through the applicator tip. Suitable accelerators include detergent compositions; surfactants, amines, urea, phosphines, alcohols, inorganic bases and salts, sulfur compounds, polymeric cyclic ethers, crown ethers, calixarenes, cyclic and acyclic carbonates, organometallics, and radical. The polymerizable material may also contain an initiator which is inactive until activated by a catalyst in the applicator tip. Initiators activated by stimulation such as heat and/or light are also suitable if the tip and/or applicator is appropriately subjected to such stimulation.

U.S. Pat. Application No. 20050196431 to Narang et al. discloses an applicator tip for an applicator for applying a polymerizable monomeric adhesive composition that can include a bioactive material, a flavorant, a polymerization initiator, and/or a polymerization rate modifier. It has been discovered that the use of methanol, alone or as a component of a mixture of low boiling point solvents, to apply a polymerization accelerator to an applicator tip used to dispense monomer-containing adhesive compositions, provides an unexpectedly superior distribution profile of the material on, and within, the applicator tip. Applicator tips according to their invention can control the setting time of the polymerized or cross-linked adhesive, extend the shelf life of the monomer and control the flow properties of applied cyanoacrylate adhesives.

U.S. Pat. No. 4,460,759 to Narang discloses two-component adhesive compositions. One component contains the cyanoacrylate monomer and the second component contains a weakly acidic or weakly basic ionic accelerator consisting of a cation having a pKa of at least 10 and a nucleophilic anion.

Another approach to enhance the cure speed of cyanoacrylate adhesive is to apply the diluted solutions of the accelerators in low-boiling point solvents to the cyanoacrylate adhesives. The accelerator solutions can be added to the substrate in advance or applied when the cyanoacrylate adhesive is still liquid. Japanese Patent Application No. JP-A-03 207 778 discloses the use of solutions of aliphatic, alicyclic and, especially, tertiary aromatic amines as the activators for the curing of cyanoacrylate adhesives. Specific examples included N,N-dimethylbenzylamine, N-methylmorpholine and N,N-diethyltoluidine. Japanese Patent Application No. JP-A-62 022 877 suggested the use of solutions of lower fatty amines, aromatic amines, and dimethylamine for the same purpose.

British Patent Specification No. 1 230 560 described cyanoacrylate adhesive compositions containing certain substituted heterocyclic compounds as accelerators. The compositions may be presented in a two-part form, the first part comprising the cyanoacrylate adhesive and the second part comprising at least one of the substituted heterocyclic compounds, preferably dissolved in an organic solvent. The heterocyclic compound is invariably present in one part of a two-part composition because iminoethylene-substituted triazines and pyrimido-pyrimidines accelerate the polymerization so rapidly that they must be kept apart from the cyanoacrylate composition before use. An effective adhesive bond is obtained. However it is not concerned with an activator which is able to initiate polymerization throughout a layer of adhesive.

U.S. Pat. No. 3,260,637 to von Bramer discloses the use of a range of organic amines as accelerators for cyanoacrylate adhesives, particularly for use on metallic and non-metallic substrates. According to the invention, a catalyst solution comprising one or more organic amines was employed in a suitable solvent to moisten the surfaces to be bonded and to catalyze the adhesive action of cyanoacrylate adhesive composition.

U.S. Pat. No. 4,042,442 to Dombroski et al. discloses the addition of a polymerization initiator such as caffeine and theobromine to a cyanoacrylate adhesive composition. The caffeine or theobromine is added to the adhesive composition in different ways. Firstly, the caffeine or theobromine is dissolved in a volatile solvent, applied to the surfaces to be joined, the volatile solvent is allowed to evaporate, and then the cyanoacrylate adhesive composition is applied to the surfaces of the substrates to be joined. Secondly, the caffeine or theobromine can be mixed with the cyanoacrylate adhesive composition by stirring just prior to application of the adhesive to the substrates to be joined. Both of these methods are inconvenient for the user because two separate solutions or two separate applications are required.

U.S. Pat. No. 5,561,198 to Huver provided an activator for cyanoacrylate adhesives based on N,N-dialkyl aniline derivatives. The activators are characterized by a molecular weight of more than 200 and by at most 3 carbon atoms for both N,N-dialkyl substituents together. Their invention also provided methods of production and use of the activator and to the combination product of the activator and the cyanoacrylate adhesive. In their inventions, the activators were tested according to criteria including reactivity, cure rate on activated aluminum test strips, cure rate after activation, tensile shear strength on sand-blasted aluminum strips, transparency, and odor of the reactivity.

U.S. Pat. No. 6,547,917 to Hanns et al. revealed the accelerated curing of cyanoacrylate adhesives using organic compounds containing the structural element —N═C—S—S—C═N— in dilute solution as activators. Examples of such compounds include 6,6'-dithiodinicotinic acid, dibenzodiazyl disulfide, 2,2'-dipyridyl disulfide or bis(4-t-butyl-1-isopropyl-2-imidazolyl)disulfide. According to their invention, the activators are dissolved in readily volatile solvents, such as hydrocarbons, carboxylic acid esters, ketones, ethers or halogenated hydrocarbons. The activator solutions according to their invention are suitable for the accelerated curing of all conventional cyanoacrylate adhesives which contain as the fundamental constituent one or more cyanoacrylic acid esters, inhibitors of free-radical polymerization, inhibitors of anionic polymerization and, optionally, conventional auxiliary substances employed in such adhesive systems. As compared with the known accelerators, their method provided the following advantage: good accelerating action, but they nevertheless require a long waiting time between application of the activator and application of the adhesive.

U.S. Pat. No. 6,995,227 to Ryan et al. discloses an activator composition for the accelerated curing of cyanoacrylate adhesives, wherein the activator comprises a member selected from the group consisting of: aromatic heterocyclic compounds having at least one N hetero atom in the ring(s) such as pyridines, quinolines and pyrimidines and substituted on the ring(s) with at least one electron-withdrawing group which decreases the base strength of the substituted compound compared to the corresponding unsubstituted compound, mixtures of any of the foregoing with each other, and/or with N,N-dimethyl-p-toluidine, and mixtures of any of the foregoing and/or N,N-dimethyl-p-toluidine with an organic compound containing the structural element, such as dibenzothiazyl disulfide, 6,6'-dithiodinicotinic acid, 2,2'-dipyridyl disulfide, and bis(4-t-butyl-1-isopropyl-2-imidazolyl)disulfide. An activator composition may comprise a solution of one or more activators in a solvent mixture which comprises a volatile hydrocarbon and a cyclic ketone. Their invention reduced the problem of "halo" effect and provided activator solutions with different properties.

In order to improve the cure speed of cyanoacrylate adhesives, another important method is to incorporate accelerators directly to the adhesive formulations. DE-A-40 09 621 proposed the use of certain cyclodextrin derivatives as an additive to improve the cure speed of cyanoacrylate adhesive, some of which are soluble in cyanoacrylates. GB-A-2 200 124 revealed the use of acyclic phenol-formaldehyde oligomers as an accelerating additive for cyanoacrylate adhesive formulations.

German patent DE-A-22 61 261 proposed accelerator substances containing the structural element-N═C—S—. According to their invention, cyanoacrylate adhesives containing such accelerators do in fact show that even relatively large amounts of adhesive harden relatively rapidly and reliably. However, that compound has a very high volatility, so that activator solutions based thereon are unsuitable for application beforehand since the active ingredient also evaporates off with the solvent.

U.S. Pat. No. 4,386,193 to Reich, et al. discloses a rapid-setting .alpha.-cyanoacrylate based adhesive composition having good storage stability and, in particular, to an adhesive composition having a very fast setting time on wood and other substrates with a parous/acid surface by using 3 or 4 arm polyol pod and compounds as accelerators.

Japanese Patent Application No. 59-66471 discloses amine derivatives as a curing accelerator of cyanoacrylate adhesives. The amine compounds have a boiling point of between 50° C. and 250° C. Examples of suitable amines include propanolamine triethylamine, diethylamine, isopropyl amine, butyl amine, tributyl amine, N,N-dimethyl-o-toluidine, N,N-dimethyl aniline, N,N-diethyl aniline, N,N-dimethyl-p-toluidine, N,N-dimethyl-m-toluidine dimethyl benzyl amine, pyridine, picaline, vinyl pyridine, ethanolamine, and ethylene diamine U.S. Pat. No. 4,377,490 to Shiraishi et al., discloses mixtures of aromatic and aliphatic polyols and polyethers to improve initial strength of cyanoacrylate wood bonding products.

European Patent Specification No. 0 271 675 A2 discloses a primer for cyanoacrylate resin compositions for use in bonding non-polar or highly crystallized resins such as polyolefins, polyethyleneterephthalates, nylons, fluorine-containing resins, and soft PVC films. The primer comprises (i) an organic amine and (ii) a compound selected from the group consisting of benzene ring compounds having aldehyde group and nitrogen or oxygen atom-containing heterocyclic compounds having aldehyde group. The specification states that a cyanoacrylate adhesive exhibited a strong bonding strength at ambient temperature.

U.S. Pat. No. 4,718,966 to Stephen, et al. discloses cyanoacrylate adhesive compositions which employ calixarene compounds as accelerators give substantially reduced fixture and cure times on deactivating substrates such as wood, leather, ceramic, plastics and metals. The calixarene compounds are preferably employed at levels of about 0.1-1% by weight of the composition.

In U.S. Pat. No. 4,170,585 to Motegi et al., certain polyethylene glycols poly(ethyleneoxy) functional are disclosed to be additives for increasing the curing speed of cyanoacrylate compositions. Such compounds, however, have the reported disadvantage that they contain water and other substances difficult to remove which spontaneously initiate polymerization of the cyanoacrylate monomer.

Japanese Patent Application No. 8-310136 to Ohashi, et al. discloses 2-cyanoacrylate adhesive compositions containing a crown ether curing accelerator or a polyalkylene oxide curing accelerator. However, these compositions are not suitable for medical applications.

In general, cyanoacrylate combinations with accelerators have been obtainable by separately housing the cyanoacrylate and accelerator. The cyanoacrylate is then flowed past the accelerator housing to add the accelerator to the cyanoacrylate. This method is used for industrial applications, where large batches of the cyanoacrylate are needed. This method is not suitable for medical use, nor are the cyanoacrylate compositions prepared from this method amenable to being sterilized in preparation for medical use.

Based on the descriptions above, different design systems and a variety of chemicals have been applied to accelerate the curing speed of cyanoacrylate adhesives. However, most of the employed accelerators exhibited their own shortcomings at different extents. Some of them are more toxic, while others exhibit weak activation, less bond strength, high volatility and odor. In addition, irregular structure is formed in some cases, which destroys transparency of film. These disadvantages thus limit the application of cyanoacrylate adhesives in different fields, especially for medical use. The goal of the present invention is, therefore, to develop a new accelerating agent for cyanoacrylate adhesives, which is particularly suitable for medical applications.

BRIEF SUMMARY OF THE INVENTION

The present invention provides for a sterilized cyanoacrylate adhesive composition including a cyanoacrylate composition and a cure speed enhancer, wherein the sterilized cyanoacrylate adhesive composition does not cure upon sterilization.

The present invention also provides for a kit for applying the sterilized cyanoacrylate adhesive composition, including the cyanoacrylate adhesive composition and an applicator.

The present invention provides for a method of making the sterilized cyanoacrylate adhesive composition by adding a cure speed enhancer to a cyanoacrylate adhesive composition and sterilizing the composition.

The present invention further provides for a method of applying the sterilized cyanoacrylate adhesive composition to tissue by applying the sterilized cyanoacrylate adhesive composition as a liquid, and quickly curing the sterilized cyanoacrylate adhesive composition.

The present invention also provides for a method of sealing tissue by applying the sterilized cyanoacrylate adhesive composition as a liquid to tissue to be sealed, quickly curing the sterilized cyanoacrylate adhesive composition, and sealing the tissue.

DETAILED DESCRIPTION OF ILLUSTRATIVE EMBODIMENTS

The present invention provides for a sterilized cyanoacrylate adhesive composition and method of preparing the same including a cure speed enhancer added to a cyanoacrylate adhesive composition. The sterilized cyanoacrylate adhesive composition is essentially a bioabsorbable tissue adhesive for sealing and aiding in the repair of tissue. Importantly, the sterilized cyanoacrylate adhesive composition does not cure upon sterilization.

It is the goal of the present invention to provide a sterilized cyanoacrylate adhesive composition with a very fast curing speed. This is achieved by including a cure speed enhancer, preferably 18-crown-6, which is a crown ether, in the preferable amount of 100-1600 ppm, to the cyanoacrylate adhesive composition before sterilization of the composition. Any other suitable cure speed enhancer, such as, but not limited to, another crown ether, can also be used. The cure time of cyanoacrylate composition can be improved up to 2-5 times depending upon the amount of the accelerator applied. The cure speed enhancer is soluble in the cyanoacrylate monomer at room temperature. The compositions produced, packaged and sterilized according to the current invention have a much faster cure speed compared to cyanoacrylate adhesive compositions of the prior art.

The reason crown ether was chosen as the preferred cure speed enhancer, or accelerating agent, for cyanoacrylate adhesive is not only due to its excellent activation for curing. Although crown ethers are not known to possess medicinal properties themselves, they may improve drug uptake and transport properties. For example, crown ethers affected the uptake of pirarubicin by drug-resistant cells. (*Biochem. Pharmacal.* 1995, 50, 2069-2076; Curr. Med. Chem. 2001, 8, 51-64). The special complexing properties of crown ethers have led to applications in drug delivery systems and as targeting functionalities incorporated in drug derivatives and DNA-binding agents. It was shown in DNA binding studies that the positive charge of cation-crown ether complexes increases the affinity of crown ether linked compounds with the polyanionic phosphate backbone of DNA. Thus, crown ether derivatized drugs may gain an increased interaction with DNA by the formation of cationic complexes with ions that are abundant in cells, such as sodium or potassium. (Int. J. Pharm. 1997, 159, 207-213; Int. J. Pharm. 1998, 172, 33-70; Bioorg. Med. Chem. Lett. 1994, 4, 1123-1126.)

Another object of the present invention is to maintain, if not improve, the stability of cyanoacrylate adhesive compositions. As the cure speed of cyanoacrylate adhesive compositions has been dramatically improved herein, the stability of the adhesive is still conserved. Such stability of the adhesive is sustained due to the following treatments: (a) reducing the amount of contaminants and extraneous additives by applying the particulate agent, (b) providing a stable cyanoacrylate adhesive composition by use of the combination of free radical stabilizer and anionic stabilizing agent and (c) further stabilizing the cyanoacrylate adhesive composition by applying more anionic stabilizer. Even with the presence of the cure speed enhancer, the cyanoacrylate adhesive composition does not actually cure until it has been applied to tissue.

The stability of the cyanoacrylate adhesive composition with the cure speed enhancer is confirmed by both real time and accelerated aging test detailed in the Examples below. Both the set time and viscosity data indicate the stability of the said cyanoacrylate adhesive composition, also detailed below.

The amount of cure speed enhancer that is added to the monomer composition depends upon the original cure speed of cyanoacrylate monomer. The cure speed enhancer is preferably present in the amount of about 2-3200 ppm by weight of the adhesive composition. In preferred embodiments, the cure speed enhancer is present in the amount of about 40-1600 ppm, and more preferably about 100-1000 ppm of the adhesive composition. The amount of the cure speed enhancer to be used can be determined by one of ordinary skill in the art using known techniques without undue experimentation.

Preferably, the cyanoacrylate adhesive composition contains 2-octyl cyanoacrylate. The cyanoacrylate composition can have a composition as described in U.S. Provisional Application Nos. 60/858,853 and 60/892,357, i.e. a blend of cyanoacrylate with a low molecular weight polyether such as polyethylene glycol (PEG). The exact percentage of each of the components can be readily determined by one skilled in the art. The cyanoacrylate composition is bioabsorbable and degrades in the body.

The cyanoacrylate adhesive composition has a viscosity in the range from 2.5 to 70 centipoise, and preferably 5-30 centipoise, as measured with a Brookfield Viscometer at 25° C. Additionally, the viscosity of the composition should be maintained or increased by a controlled and acceptable amount after sterilization.

The cure time of cyanoacrylate adhesives in the absence of the cure speed enhancer is up to 90 seconds depending upon the amount of free radical and anionic stabilizers included. However, the cure speed is dramatically increased after applying the cure speed enhancer to the cyanoacrylate composition. An increase of up to a few seconds can be achieved depending on the amount of the cure speed enhancer applied.

According to embodiments of the present invention, the stability, and thus the shelf-life, of the cyanoacrylate adhesive compositions in the presence of the cure speed enhancer can be maintained during the accelerated aging, the packaging and sterilizing procedures. In preferred embodiments, there is substantially no initiation of polymerization of monomeric liquid adhesive compositions that affects the utility of the monomer caused by the sterilization process.

The accelerated aging test of cyanoacrylate adhesive composition was performed in the oven at 80° C. for a period of 12 days. Based on the calculation, 12 days accelerated aging at 80° C. is equal to 2 years of shelf life, and 1 day of accelerated aging at 80° C. is equal to 60.8 days. Throughout the entire aging procedure, all cyanoacrylate adhesive samples remained fluid consistency and in good color. The stability of the aged cyanoacrylate adhesive samples was confirmed by set time and viscosity test.

The viscosity of the cyanoacrylate adhesive composition with the cure speed enhancer increased as the accelerated aging proceeded but the viscosity of the aged sample after day 12 was in the acceptable range. As an example, the average viscosity of cyanoacrylate adhesive composition in the presence of the cure speed enhancer at accelerated aging day 0, day 3, day 6, day 9, and day 12 was 4.29, 5.72, 10.6, 25.5, and 53.1 centipoise, respectively.

The cure time of the cyanoacrylate adhesive composition with cure speed enhancer varied a little after the 12 days aging at 80° C. However, the cure time of the cyanoacrylate adhesive composition in the absence of the cure speed enhancer might be dropped a lot during the accelerated aging process. For example, the average set time of one adhesive made from 2-octyl cyanoacrylate was increased from 40 seconds before the accelerated aging to 65 and 112 seconds at day 6 and day 12, respectively.

The preferred free radical stabilizer included in the cyanoacrylate adhesive composition is butylated hydroxyl anisole (BHA), and the preferred anionic vapor phase stabilizer is sulfur dioxide. However, any other suitable free radical stabilizer and anionic vapor phase stabilizer can be used that are known in the art. The amount of anionic vapor phase stabilizer that is added to the monomer composition depends on the amount of cure speed enhancer applied, the monomer to be stabilized, as well as the packaging material to be used for the composition. Preferably, the anionic vapor phase stabilizer is added to give a concentration of less than 20 parts per million (ppm). The amount to be used can be determined by one of ordinary skill in the art using known techniques without undue experimentation.

Vinyl pyrrolidone polymers and copolymers can be applied to reduce the amount of contaminants and extraneous additives in the resulting adhesives from the cyanoacrylate adhesive formulation. These particulate agents are combined with the monomer adhesive in mutual contact until the adhesive is destabilized, whereupon the adhesive becomes isolated from the destabilizing agent by various means such as to effect isolation of the adhesive from the destabilizing component. It is only a requisite that enough excess stabilizer is left behind so as to provide the desirable speed of cure.

The purity of cyanoacrylate adhesive compositions was checked by GC-MS. More than 99% of the adhesive composition is 2-octyl cyanoacrylate. No plasticizer or thixotropic agent is incorporated in the said cyanoacrylate adhesive composition.

The cyanoacrylate adhesive compositions are sterilized. This is one novel aspect of the invention, as prior cyanoacrylate compositions with accelerators were not sterilized for medical use. The sterilization can be accomplished by common techniques, and is preferably accomplished by methods including, but not limited to, chemical, physical, and irradiation methods. Examples of chemical methods include, but are not limited to, exposure to ethylene oxide. Examples of irradiation methods include, but are not limited to, gamma irradiation, electron beam irradiation, and microwave irradiation. Preferred methods are chemical sterilization and electron beam sterilization. Also, the cyanoacrylate compositions can be sterilized with ultraviolet (UV) radiation. Further, upon sterilization with any of these methods, the cyanoacrylate adhesive compositions are not cured. In other words, curing does not occur until application to tissue.

The sterility of the cyanoacrylate monomer composition with the cure speed enhancer was analyzed by Bacteriostasis and Fungistasis tests. The test sample consisted of the sample with a puncture created to allow the liquid inside of the sample to mix with the test media. All were immersed into 500 ml of Soybean Casein Digest Medium (SCDM). The test microorganism such as *Bacillus subtilis, Candida albicans*, and *Aspergillus niger*, at less than 100 colony forming units, was inoculated into each of the test sample containers and into a positive control container of the same medium. After inoculation, the test sample and positive control container were incubated at 20-25° C. for a five day maximum incubation period. The growth of *Bacillus subtilis, Candida albicans*, and *Aspergillus niger* was observed for the said cyanoacrylate adhesive before the sterilization, while the said adhesives after sterilization exert a gross fungistatic effect on *Bacillus subtilis, Candida albicans*, and *Aspergillus niger*.

Bond strength and wound closure were analyzed for the cyanoacrylate adhesive composition with the cure speed enhancer. The average bond strength from tensile shear method (metal to metal) for the compositions is 107.86 lbs/cm$^2$ with a standard deviation 13.03 lbs/cm$^2$.

In vivo biomechanical evaluation was performed using the rat linear incision wound model in order to assess and evaluate the efficacy of the cyanoacrylate composition with the cure speed enhancer as a new topical surgical tissue adhesive for the application of incisional wound closure. For direct comparison, the commercially available product Dermabond was also evaluated. The male Sprague-Dawley rat was chosen as the animal model and this animal model has been used extensively for incisional wound strength studies, which has been well documented in the literature. All study animals were acclimatized to their designated housing for approximately 7 days prior to the day of treatment. Prior to surgery, final selection of the animals was based on a visual appraisal of good clinical condition, and body weight specifications.

TABLE 1

Biomechanical wound strength results for the cyanoacrylate
adhesive with the cure speed enhancer and Dermabond.

| Date | Study Time Point | Animal | Study Group | Group Description | Side L/R |
|---|---|---|---|---|---|
| May 8, 2006 | acute 1 | A | DERMABOND* HV | (Lot# 125241 Exp. 2007-12) | L |
| May 8, 2006 | acute 2 | A | DERMABOND* HV | (Lot# 125241 Exp. 2007-12) | R |
| May 8, 2006 | acute 3 | A | DERMABOND* HV | (Lot# 125241 Exp. 2007-12) | L |
| May 8, 2006 | acute 4 | A | DERMABOND* HV | (Lot# 125241 Exp. 2007-12) | R |
| May 8, 2006 | acute 5 | A | DERMABOND* HV | (Lot# 125241 Exp. 2007-12) | L |
| May 8, 2006 | acute 6 | A | DERMABOND* HV | (Lot# 125241 Exp. 2007-12) | R |
| May 8, 2006 | acute 7 | A | DERMABOND* HV | (Lot# 125241 Exp. 2007-12) | L |
| May 8, 2006 | acute 8 | A | DERMABOND* HV | (Lot# 125241 Exp. 2007-12) | R |
| May 8, 2006 | acute 9 | A | DERMABOND* HV | (Lot# 125241 Exp. 2007-12) | L |
| May 8, 2006 | acute 10 | A | DERMABOND* HV | (Lot# 125241 Exp. 2007-12) | R |
| May 8, 2006 | acute 11 | A | DERMABOND* HV | (Lot# 125241 Exp. 2007-12) | L |
| May 8, 2006 | acute 12 | A | DERMABOND* HV | (Lot# 125241 Exp. 2007-12) | R |
| May 8, 2006 | acute 13 | A | DERMABOND* HV | (Lot# 125241 Exp. 2007-12) | L |
| May 8, 2006 | acute 14 | A | DERMABOND* HV | (Lot# 125241 Exp. 2007-12) | R |
| May 8, 2006 | acute 1 | B | Spartan Medical Liquid Advesive Bandage | (Lot# 327) | R |
| May 8, 2006 | acute 2 | B | Spartan Medical Liquid Advesive Bandage | (Lot# 327) | L |
| May 8, 2006 | acute 3 | B | Spartan Medical Liquid Advesive Bandage | (Lot# 327) | R |
| May 8, 2006 | acute 4 | B | Spartan Medical Liquid Advesive Bandage | (Lot# 327) | L |
| May 8, 2006 | acute 5 | B | Spartan Medical Liquid Advesive Bandage | (Lot 327) | R |
| May 8, 2006 | acute 6 | B | Spartan Medical Liquid Advesive Bandage | (Lot 327) | L |
| May 8, 2006 | acute 7 | B | Spartan Medical Liquid Advesive Bandage | (Lot 327) | R |
| May 8, 2006 | acute 8 | B | Spartan Medical Liquid Advesive Bandage | (Lot# 327) | L |
| May 8, 2006 | acute 9 | B | Spartan Medical Liquid Advesive Bandage | (Lot# 327) | R |
| May 8, 2006 | acute 10 | B | Spartan Medical Liquid Advesive Bandage | (Lot# 327) | L |
| May 8, 2006 | acute 11 | B | Spartan Medical Liquid Advesive Bandage | (Lot# 327) | R |
| May 8, 2006 | acute 12 | B | Spartan Medical Liquid Advesive Bandage | (Lot# 327) | L |
| May 8, 2006 | acute 13 | B | Spartan Medical Liquid Advesive Bandage | (Lot# 327) | R |
| May 8, 2006 | acute 14 | B | Spartan Medical Liquid Advesive Bandage | (Lot# 327) | L |

| Date | Wound Size | Termination Weight (g) | Ultimate Pressure (mmHg) | Comments |
|---|---|---|---|---|
| May 8, 2006 | 1 | 275 | 271 | |
| May 8, 2006 | 1 | 297 | 230 | |
| May 8, 2006 | 1 | 286 | 291 | |
| May 8, 2006 | 1 | 285 | 163 | |
| May 8, 2006 | 1 | 290 | 226 | |
| May 8, 2006 | 1 | 297 | 169 | |
| May 8, 2006 | 1 | 280 | 162 | |
| May 8, 2006 | 1 | 277 | 200 | |
| May 8, 2006 | 1 | 294 | 161 | |
| May 8, 2006 | 1 | 284 | 276 | |
| May 8, 2006 | 1 | 282 | 320 | |
| May 8, 2006 | 1 | 287 | 105 | |
| May 8, 2006 | 1 | 280 | 326 | |

TABLE 1-continued

Biomechanical wound strength results for the cyanoacrylate adhesive with the cure speed enhancer and Dermabond.

| May 8, 2006 | 1 | 205 | 372 |
|---|---|---|---|
|  | Mean | 255.5 | 240.0 |
|  | St. Dev. | 5.3 | 70.1 |
| May 8, 2006 | 1 | 275 | 210 |
| May 8, 2006 | 1 | 297 | 220 |
| May 8, 2006 | 1 | 286 | 164 |
| May 8, 2006 | 1 | 285 | 215 |
| May 8, 2006 | 1 | 290 | 119 |
| May 8, 2006 | 1 | 287 | 274 |
| May 8, 2006 | 1 | 280 | 314 |
| May 8, 2006 | 1 | 277 | 243 |
| May 8, 2006 | 1 | 294 | 251 |
| May 8, 2006 | 1 | 284 | 235 |
| May 8, 2006 | 1 | 282 | 291 |
| May 8, 2006 | 1 | 287 | 261 |
| May 8, 2006 | 1 | 280 | 285 |
| May 8, 2006 | 1 | 292 | 175 |
|  | Mean | 255.5 | 231.7 |
|  | St. Dev. | 6.3 | 52.5 |
|  |  |  | p-value |
|  | ANOVA (p = 0.05) |  | 0.736201604 |

The animals were anesthetized, placed on a surgical table with a water-heating pad, and prepped with Betadine surgical skin prep and 70% alcohol solution. To control incision length and location, a template and surgical skin-marking pen were used to mark two symmetric 0.75-inch linear incisions over each dorsolateral flank area. All animals underwent the same surgical procedure. All incisions were made by the same surgeon and extend through the skin, subcutaneous tissue and panniculus carnosus. The incisional wounds were then biomechanically tested for incisional wound strength.

A BTC disposable acrylic test ring (ID 2.5 cm) was placed around the wound and secured to the skin using cyanoacrylate adhesive with the cure speed enhancer or commercially available Dermabond. A small amount of perfluorinated grease was applied to the top of the ring interface to assure a tight vacuum seal. The BTC-2000™ test chamber was integrated with the test ring until the chamber and ring were securely interconnected. The test chamber was held by hand comfortably to assure that no positive force was being exerted on the wound. A constant negative pressure was applied to the wound at a rate of 10 mmHg/second, producing a multi-axial stress on the wound. A displacement laser captured displacement of wound margins.

Based on the wound strength raw data presented in Table 1, the average ultimate pressure applied in wound site for the said cyanoacrylate adhesive and the commercial Dermabond was in the same level, indicating the cyanoacrylate with the cure speed enhancer possesses a bond strength strong enough to be used for wound closure as a medical product.

In vitro cytotoxicity of the cyanoacrylate adhesive with the cure speed enhancer was evaluated. For comparison, the commercially available product Dermabond was also evaluated. A 2 cm² sterile disc of filter paper was saturated with 2-octylcyanoacrylate adhesive composition with the cure speed enhancer prior to dosing. L 929 mammalian fibroblast cell, seeded at a density of about 100,000 cells per mL at 7 mL per 60×15 mm plate, were allowed to propagate in serum supplemented minimum essential medium in a single test plate until greater than 80% confluence was observed. Growth generally requires about 48 to 72 hours in a humidified carbon dioxide incubator at 37±1° C. When the cell culture reached confluence, the growth media was removed aseptically and triplicate plates were refilled with serum supplemented culture media containing not more than 2% agar overlay. The flat surface of the cyanoacrylate adhesive sample, positive and negative controls, and media control was then placed in contact with solidified agar surface. The test plates were then returned to the incubator for 24 hours. At the end of the additional incubation, the plates were individually observed under an inverted light microscope for signs of cell toxicity. The test results (Table 2) indicated that only minimal cytotoxicity was observed for the cyanoacrylate adhesive with the cure speed enhancer, while minimal to mild cytotoxicity was observed for the control Dermabond.

TABLE 2

Results of test for in vitro cytotoxicity.

| Test article | Evaluation of cytotoxicity |
|---|---|
| The said adhesive | ±, ±, ± |
| Dermabond | ±, ±, 1 |
| USP HOPERS (Negative control) | 0, 0, 0 |
| USP Bioreaction RS (Positive control) | 2, 2, 2 |
| Media Control (MEM) | 0, 0, 0 |

Ratings

| | | |
|---|---|---|
| 0 | Noncytotoxic | No detectable zone around or under specimen |
| ± | Slight cytotoxic | Some malformed or degenerated cells under specimen |
| 1 | Mildly cytotoxic | Zone limited to area under specimen |
| 2 | Moderate cytotoxic | Zone extends 0.5 to 1.0 cm beyond specimen |
| 3 | Severely cytotoxic | Zone extends greater than 1.0 cm beyond specimen |

The above results of the in vivo biomechanical evaluation using the rat linear incision wound model revealed that the cyanoacrylate adhesive has comparable bond strength as the commercial product Dermabond. In addition, in vitro cytotoxicity provided additional evidence that the cyanoacrylate adhesive is more suitable for medical use. The cyanoacrylate adhesive exhibits only minimally cytotoxicity, while minimally to mild cytotoxicity was observed for the control Dermabond. Therefore, the cyanoacrylate adhesive of the present invention has advantages over the prior art.

The cyanoacrylate composition of the present invention can be used in conjunction with the inventions disclosed in U.S. Provisional Application No. 60/858,853 and 60/892,357, incorporated by reference herein. For example, the cyanoacrylate composition of the present invention can be used in conjunction with therapeutic-loaded nanoparticles to provide further therapeutic relief.

The cyanoacrylate compositions of the present invention are especially suitable for use in medical applications. In use, the cyanoacrylate adhesive composition is applied to the desired tissue area as a liquid which then polymerizes upon contact with tissue. The cure speed enhancer allows for quick polymerization and setting of the cyanoacrylate adhesive composition, i.e. quick curing. The polymerized patch of cyanoacrylate adhesive allows the tissue to heal properly. Over time, water is drawn into the adhesive, causing it to degrade. The components of the adhesive then are cleared from the body.

The present invention further provides for a kit for applying the cyanoacrylate adhesive composition of the present invention, including an applicator containing therein an effective amount of the cyanoacrylate composition. The applicator can be any suitable applicator such as, but not limited to, Q-tips, a swab, or an applicator tip on a container with the cyanoacrylate composition therein. The kit can further contain directions for application. When the present invention is used with other therapeutics, separate containers can be provided for the cyanoacrylate composition and the therapeutic for application.

Individual applicators can be packaged separately to maintain sterile conditions. For example, each applicator can be packaged in plastic or any other suitable enclosing material. Multiple applicators can then be packaged in a box for shipping.

The compound of the present invention is administered and dosed in accordance with good medical practice, taking into account the clinical condition of the individual patient, the site and method of administration, scheduling of administration, patient age, sex, body weight and other actors known to medical practitioners. The pharmaceutically, "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered in any suitable way. Implants of the compounds are also useful. The patients being treated are warm-blooded animals and, in particular, mammals including human beings. The pharmaceutically acceptable carriers, diluents, adjuvants and vehicles as well as implant carriers generally refer to inert, nontoxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicles, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those disclosed in U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

While specific embodiments are disclosed herein, they are not exhaustive and can include other suitable designs and systems that vary in designs, methodologies, and transduction systems (i.e., assays) known to those of skill in the art. In other words, the examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

197.4 g of 2-octyl cyanoacrylate was mixed with 0.20 g of poly vinyl pyrrolidone (PVP) under vacuum for 2 hours and solid powder was removed by filtration. The resulting solution was mixed with certain amounts of stabilizer, BHA, and colorant, D & C Violet under vacuum for a minimum of 0.5 hour. A sulfur dioxide solution in 2-octyl cyanoacrylate was charged into the solution to further stabilize the cyanoacrylate composition. The resulting purple solution was then filtered with a micrometer filter to yield the activated 2-octyl cyanoacrylate adhesive composition.

EXAMPLE 2

27 pounds of the activated 2-octyl cyanoacrylate was charged into stainless steel container equipped with the mechanical agitator. 0.12 g of $SO_2$ solution (5.8%) in 2-octyl cyanoacrylate was added to the container and stirred for a minimum of 0.5 hour. 3.3 g of 18-crown-6 was dissolved in 30 mL of 2-octyl cyanoacrylate in microwave, which was added to the bulk solution of 2-octyl cyanoacrylate in the stainless steel container and stirred for a minimum of 0.5 hour. After the filtration, the resulting cyanoacrylate adhesive composition was subjected to viscosity, set time, bond strength and accelerated aging tests (see Table 3). The bond strength measured for the samples at day 0 and day 12 are 773.9, and 723.2 lbs/inch² respectively.

TABLE 3

Set time and viscosity results of examples 2 and 3.

|  | Aging condition | Day 0 | | Day 5 | | Day 9 | | Day 12 | |
| --- | --- | --- | --- | --- | --- | --- | --- | --- | --- |
|  |  | Set time (s) | Viscosity (cps) | Set time (s) | Viscosity (cps) | Set time (s) | Viscosity (cps) | Set time (s) | Viscosity (cps) |
| Example 2 | 12 days 80° C. | 22 | 4.35 | 20 | 4.56 | 18 | 4.78 | 28 | 5.65 |
| Example 3 | 12 days 80° C. | 35 | 5.43 | 33 | 4.99 | 24 | 6.30 | 38 | 6.52 |

EXAMPLE 3

18 pounds of the activated 2-octyl cyanoacrylate was charged into stainless steel container equipped with the mechanical agitator. 0.078 g of $SO_2$ solution (5.8%) in 2-octyl cyanoacrylate was added to the container and stirred for a minimum of 0.5 hour. 1.5 g of 18-crown-6 was dissolved in 30 mL of 2-octyl cyanoacrylate in microwave, which was added to the bulk solution of 2-octyl cyanoacrylate in the stainless steel container and stirred for a minimum of 0.5 hour. After the filtration, the resulting cyanoacrylate adhesive composition was subjected to viscosity, set time, bond strength and accelerated aging tests (see Table 3). The bond strength measured for the samples at day 0 and day 12 are 714.5, and 703.1 lbs/inch², respectively.

EXAMPLE 4

864.4 g of the activated 2-octyl cyanoacrylate was put into 1 L of opaque polyethylene bottle. 0.142 g of $SO_2$ solution (5.8%) in 2-octyl cyanoacrylate was added to the container and stirred for a minimum of 1 hour.

EXAMPLE 5

To a polyethylene bottle, 30.8 g of 2-octyl cyanoacrylate from example 4 was mixed with 98.6 mg of 18-crown-6 and stirred at room temperature for 2 hours. The sample was subjected to the accelerated aging test at 80° C. The average set time for the samples at day 0, day 6, and day 12 are 6.7, 7.3, and 9.4 s, respectively. The average viscosity for the samples at day 0, day 6, and day 12 are 3.27, 2.86, and 28.8 cps, respectively.

EXAMPLE 6

To a polyethylene bottle, 30.1 g of 2-octyl cyanoacrylate from example 4 was mixed with 72.4 mg of 18-crown-6 and stirred at room temperature for 2 hours. The sample was subjected to the accelerated aging test at 80° C. The average set time for the samples at day 0, day 6, and day 12 are 8.3, 9, and 14 s, respectively. The average viscosity for the samples at day 0, day 6, and day 12 are 2.86, 2.86, and 24.3 cps, respectively.

EXAMPLE 7

To a polyethylene bottle, 30.9 g of 2-octyl cyanoacrylate from example 4 was mixed with 30.9 mg of 18-crown-6 and stirred at room temperature for 2 hours. The sample was subjected to the accelerated aging test at 80° C. The average set time for the samples at day 0, day 6, and day 12 are 14.7, 14.7, and 19.3 seconds, respectively. The average viscosity for the samples at day 0, day 6, and day 12 are 3.06, 3.06, and 20.4 cps, respectively.

EXAMPLE 8

To a polyethylene bottle, 30.5 g of 2-octyl cyanoacrylate from example 4 was mixed with 21.4 mg of 18-crown-6 and stirred at room temperature for 2 hours.

EXAMPLE 9

In a polyethylene bottle, 4.4 g of 2-octyl cyanoacrylate composition from example 8 was diluted to 30.8 g by 2-octyl cyanoacrylate composition from example 4 and stirred at room temperature for 2 hours. The sample was subjected to the accelerated aging test at 80° C. The average set time for the samples at day 0, day 6, and day 12 are 33, 35.3, and 39 seconds, respectively. The average viscosity for the samples at day 0, day 6, and day 12 are 2.65, 2.65, and 9.19 cps, respectively.

EXAMPLE 10

In polyethylene bottle, 0.616 g of 2-octyl cyanoacrylate composition from example was diluted to 30.8 g by 2-octyl cyanoacrylate composition from example 4 and stirred at room temperature for 2 hours. The sample was subjected to the accelerated aging test at 80° C. The average set time for the samples at day 0, day 6, and day 12 are 70.3, 73.7, and 75 seconds, respectively. The average viscosity for the samples at day 0, day 6, and day 12 are 2.87, 2.65, and 3.06 cps, respectively.

EXAMPLE 11

473.4 g of the activated 2-octyl cyanoacrylate was put into 1 L of opaque polyethylene bottle. 4.5 mg of $SO_2$ solution (5.8%) in 2-octyl cyanoacrylate was added to the container and stirred for a minimum of 1 hour.

EXAMPLE 12

To a polyethylene bottle, 30.1 g of 2-octyl cyanoacrylate from example 11 was mixed with 96.5 mg of 18-crown-6 and stirred at room temperature for 2 hours. The sample was subjected to the accelerated aging test at 80° C. The average set time for the samples at day 0, day 6, and day 12 are 6.7, 6.3, and 7.7 seconds, respectively. The average viscosity for the samples at day 0, day 6, and day 12 are 2.86, 3.47, and 11.4 cps, respectively.

EXAMPLE 13

To a polyethylene bottle, 30.1 g of 2 octyl cyanoacrylate from example 11 was mixed with 48.3 mg of 18-crown-6 and stirred at room temperature for 2 hours. The sample was subjected to the accelerated aging test at 80° C. The average set time for the samples at day 0, day 6, and day 12 are 10, 9.7, and 11 seconds, respectively. The average viscosity for the samples at day 0, day 6, and day 12 are 3.06, 3.27, and 7.33 cps, respectively.

EXAMPLE 14

To a polyethylene bottle, 29.9 g of 2-octyl cyanoacrylate from example 11 was mixed with 29.9 mg of 18-crown-6 and stirred at room temperature for 2 hours. The sample was subjected to the accelerated aging test at 80° C. The average set time for the samples at day 0, day 6, and day 12 are 12.7, 11, and 12.3 seconds, respectively. The average viscosity for the samples at day 0, day 6, and day 12 are 2.65, 3.24, and 3.68 cps, respectively.

EXAMPLE 15

To a polyethylene bottle, 30.0 g of 2-octyl cyanoacrylate from example 11 was mixed with 8.10 mg of 18-crown-6 and stirred at room temperature for 2 hours. The sample was subjected to the accelerated aging test at 80° C. The average set time for the samples at day 0, day 6, and day 12 are 17, 15, and 17.3 seconds, respectively. The average viscosity for the samples at day 0, day 6 and day 12 are 2.87, 2.65, and 3.27 cps, respectively.

EXAMPLE 16

To a polyethylene bottle, 19.6 g of 2-octyl cyanoacrylate from example 11 was mixed with 9.9 mg of 18-crown-6 and stirred at room temperature for 2 hours.

EXAMPLE 17

In a polyethylene bottle, 2.4 g of 2-octyl cyanoacrylate composition from example 16 was diluted to 30 g by 2-octyl cyanoacrylate composition from example 11 and stirred at room temperature for 2 hours. The sample was subjected to the accelerated aging test at 80° C. The average set time for the samples at day 0, day 6, and day 12 are 42.3, 55.3, and 47 seconds, respectively. The average viscosity for the samples at day 0, day 6, and day 12 are 2.87, 3.27, and 2.65 cps, respectively.

EXAMPLE 18

In a polyethylene bottle, 0.59 g of 2-octyl cyanoacrylate composition from example 16 was diluted to 30 g by 2-Octyl cyanoacrylate composition from example 11 and stirred at room temperature for 2 hours. The sample was subjected to the accelerated aging test at 80° C. The average set time for the samples at day 0, day 6, and day 12 are 53.7, 67, and 61.7 seconds, respectively. The average viscosity for the samples at day 0, day 6, and day 12 are 3.06, 2.87, and 3.47 cps, respectively.

EXAMPLE 19

33.4 pounds of the activated 2-octyl cyanoacrylate was charged into stainless steel container equipped with the mechanical agitator. 0.144 g of $SO_2$ solution (5.8%) in 2-octyl cyanoacrylate was added to the container and stirred for a minimum of 0.5 hour. 4.06 g of 18-crown-6 was added to the bulk solution of 2-octyl cyanoacrylate in the stainless steel container and stirred for a minimum of 0.5 hour. After the filtration, the resulting cyanoacrylate adhesive composition was subjected to viscosity, set time, bond strength and accelerated aging tests.

EXAMPLE 20

To a polyethylene bottle, 30.8 g of 2-octyl cyanoacrylate composition from example 19 was mixed with 90.5 mg of 18-crown-6 and stirred at room temperature for 2 hours. The sample was subjected to the accelerated aging test at 80° C. The average set time for the samples at day 0, day 6, and day 12 are 8.67, 11, and 11.3 seconds, respectively. The average viscosity for the samples at day 0, day 6, and day 12 are 3.06, 2.86, and 55.2 cps, respectively.

EXAMPLE 21

To a polyethylene bottle, 30.8 g of 2-octyl cyanoacrylate composition from example 19 was mixed with 41.3 mg of 18-crown-6 and stirred at room temperature for 2 hours. The sample was subjected to the accelerated aging test at 80° C. The average set time for the samples at day 0, day 6, and day 12 are 17, 24.3, and 22 seconds, respectively. The average viscosity for the samples at day 0, day 6, and day 12 are 2.45, 2.65, and 23.8 cps, respectively.

EXAMPLE 22

Shelf life (real time) of 2-octyl cyanoacrylate adhesives with cure speed enhancer is under way and set time and viscosity data have been accumulated up to 9 months. Data for 2 year shelf life will be obtained by the end of May of 2008. The average set time for the samples at month 0, month 3, month 8, and month 10 are 35, 22, 35, and 31 seconds, respectively. The average viscosity for the samples at month 0, month 3, month 8, and month 10 are 5.11, 4.49, 8.97 and 10 cps, respectively.

EXAMPLE 23

Heat of polymerization of 2-octyl cyanoacrylate adhesives with cure speed enhancer was measured with DSC. Samples were transferred to an aluminum DSC pan via disposable pipette from a freshly opened applicator. Each sample was heated from 30° C. to 300° C. at a rate of 10° C./min in an atmosphere of nitrogen flowing at a rate of 20 cc/min. In each product there appears to be a two stage polymerization which cannot be accurately separated using a temperature ramp of 10° C. per minute. The average heat of polymerization is 225 J/g.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A sterilized cyanoacrylate adhesive composition comprising
   99% or more by weight, based on the weight of the adhesive composition, of 2-octyl cyanoacrylate, mixed together with
   100 to 1000 parts per million, based on the weight of the adhesive composition, of a 18-crown-6 ether,
   a free radical stabilizer, and
   an anionic vapor phase stabilizer;
   wherein the composition is sterilized by irradiation, and the viscosity of the sterilized composition is 5 to 70 cp following storage for twelve days at 80° C.

2. The sterilized cyanoacrylate adhesive composition of claim 1, wherein the sterilized composition has a viscosity of 5 to 30 cp following storage for twelve days at 80° C.

3. The sterilized cyanoacrylate adhesive composition of claim 1, wherein the composition has been treated with a particulate agent selected from the group consisting of vinyl pyrrolidone polymers and co-polymers.

4. The sterilized cyanoacrylate adhesive composition of claim 1, wherein the anionic vapor phase stabilizer is present in the composition at a concentration of less than 20 parts per million.

5. The sterilized cyanoacrylate adhesive composition of claim 3, wherein the free radical stabilizer is butylated hydroxyl anisole and the anionic vapor phase stabilizer is sulfur dioxide.

6. The sterilized cyanoacrylate adhesive composition of claim 1, further comprising therapeutic-loaded nanoparticles.

7. The sterilized cyanoacrylate adhesive composition of claim 1, wherein the irradiation is gamma irradiation, electron beam irradiation, microwave irradiation, or ultraviolet radiation.

8. A kit, comprising the sterilized cyanoacrylate adhesive composition of claim 1 and an applicator.

9. The kit of claim 8, wherein said sterilized cyanoacrylate adhesive composition has been treated with a particulate agent selected from the group consisting of vinyl pyrrolidone polymers and co-polymers.

10. The kit of claim 8, wherein the anionic vapor phase stabilizer is present in the composition at a concentration of less than 20 parts per million.

11. The kit of claim 9, wherein the free radical stabilizer is butylated hydroxyl anisole and the anionic vapor phase stabilizer is sulfur dioxide.

12. The kit of claim 8, wherein the sterilized cyanoacrylate adhesive composition further comprises therapeutic-loaded nanoparticles.

13. A method of making the sterilized cyanoacrylate adhesive composition of claim 1, comprising
   mixing 99% or more by weight, based on the weight of the adhesive composition, of 2-octyl cyanoacrylate with a free radical stabilizer, an anionic vapor phase stabilizer, and 100 to 1000 parts per million, based on the weight of the adhesive composition, of a 18-crown-6 crown ether to form a cyanoacrylate adhesive composition, and
   sterilizing the composition by irradiating the composition, wherein the sterilized composition has a viscosity of 5 to 70 cp following storage for twelve days at 80° C.

14. The method of claim 13, wherein the sterilized composition has a viscosity of 5 to 30 cp following storage for twelve days at 80° C.

15. The method of claim 13, further comprising treating the composition with a particulate agent selected from the group consisting of vinyl pyrrolidone polymers and co-polymers.

16. The method of claim 13, wherein the anionic vapor phase stabilizer is present in the composition at a concentration of less than 20 parts per million.

17. The method of claim 15, wherein the free radical stabilizer is butylated hydroxyl anisole and the anionic vapor phase stabilizer is sulfur dioxide.

18. The method of claim 13, further comprising mixing therapeutic-loaded nanoparticles together with the cyanoacrylate adhesive composition.

19. The method of claim 13, wherein the sterilizing comprises irradiating the composition with gamma irradiation, electron beam irradiation, microwave irradiation, or ultraviolet radiation.

20. The method of claim 13, wherein the sterilizing comprises gamma irradiation.

21. A method of sealing tissue, comprising
   applying the sterilized cyanoacrylate adhesive composition of claim 1 to a patient's tissue, and
   allowing the sterilized composition to cure.

* * * * *